United States Patent [19]

Vianello et al.

[11] Patent Number: 5,086,769
[45] Date of Patent: Feb. 11, 1992

[54] TANNING CHAIR

[75] Inventors: Daniele Vianello, Milan; Hiromitsu Kawai; Antonio Ubezio, both of Novara; Orlando Jemma, Genoa, all of Italy

[73] Assignee: Whitesun S.p.A., Italy

[21] Appl. No.: 414,029

[22] Filed: Sep. 28, 1989

[30] Foreign Application Priority Data

Sep. 28, 1988 [IT] Italy .............................. 12558 A/88

[51] Int. Cl.⁵ .......................... A61N 5/06; A61H 15/02
[52] U.S. Cl. ...................................... 128/377; 128/33; 128/52; 128/46; 128/56; 297/345; 297/68
[58] Field of Search .................. 128/376, 377, 33, 52, 128/46, 56; 250/504 R; 297/78, 345, 68, 180; 381/162; 62/261

[56] References Cited

U.S. PATENT DOCUMENTS

| | | | |
|---|---|---|---|
| 481,676 | 8/1892 | Sharp | 128/202.25 X |
| 743,432 | 11/1903 | Blackmarr et al. | 128/202.25 X |
| 1,617,108 | 2/1927 | Gursky | 297/68 |
| 2,034,985 | 3/1936 | Lilley | 297/68 |
| 2,770,233 | 11/1956 | Thomas | 128/33 |
| 2,803,248 | 8/1957 | Deuser | 128/202.25 X |
| 2,834,351 | 5/1958 | Garson | 128/377 |
| 2,954,771 | 10/1960 | Boyan | 250/504 R X |
| 3,136,577 | 6/1964 | Richard | 297/180 |
| 3,880,152 | 4/1975 | Nohmura | 128/33 |
| 4,023,566 | 5/1977 | Martinmaas | 128/33 |
| 4,245,826 | 1/1981 | Wirges | 297/345 X |
| 4,258,706 | 3/1981 | Shank | 128/33 |
| 4,335,724 | 6/1982 | Frei et al. | 128/376 X |
| 4,375,812 | 3/1983 | Vaseen et al. | 128/202.25 X |
| 4,465,266 | 8/1984 | Hale | 297/345 X |
| 4,492,407 | 1/1985 | Broadhead | 297/78 |
| 4,574,786 | 3/1986 | Hashimoto et al. | 128/62 |
| 4,576,149 | 3/1986 | Otuka et al. | 128/33 |
| 4,595,838 | 6/1986 | Kerschgens | 250/504 R |
| 4,615,336 | 10/1986 | Fijimoto | 128/52 |
| 4,683,888 | 8/1987 | Kramer et al. | 128/376 |
| 4,719,764 | 1/1988 | Cook | 62/261 |
| 4,750,208 | 6/1988 | Yamada et al. | 381/162 |
| 4,785,798 | 11/1988 | Yamasaki | 128/46 |
| 4,839,513 | 6/1989 | Wijtsma | 250/504 R |
| 4,846,525 | 7/1989 | Manning | 297/180 |
| 4,866,795 | 9/1989 | Dahlqvist | 297/68 X |
| 4,881,548 | 11/1989 | Kramer | 128/376 |
| 4,923,248 | 5/1990 | Feher | 297/180 |
| 4,960,110 | 10/1990 | Yamasaki | 128/52 |
| 4,964,674 | 10/1990 | Altmann et al. | 297/180 |

FOREIGN PATENT DOCUMENTS

| | | | |
|---|---|---|---|
| 538455 | 3/1957 | Canada | 297/68 |
| 140286 | 5/1902 | Fed. Rep. of Germany | 128/377 |
| 2910865 | 3/1979 | German Democratic Rep. | 128/376 |
| 2912808 | 10/1980 | German Democratic Rep. | 128/376 |

Primary Examiner—Edgar S. Burr
Assistant Examiner—Eric P. Raciti
Attorney, Agent, or Firm—Larson and Taylor

[57] ABSTRACT

The object of the present invention is a chair characterized in that this chair can be quickly converted into a couch, by causing the back (2), the seat (3), and the foot-rest (4) thereof to be moved on to the same horizontal plane, so that tanning apparatus (31, 36, 41, 42, 43) for tanning both the body and the face and the hands of a user, can be advantageously associated therewith.

The chair according to the invention is provided with an articulated skeleton (1) for supporting the back (2), the seat (3), and the foot-rest thereof. The skeleton (1) has such linkages and kinematic connections that an uncomfortable sliding movement of a user sitting on the chair is avoided, when the angular position of the chair is being changed.

The chair according to the invention, further comprises mechanical massage means (22) which are incorporated into its back (2), and means for a passive gymnastic exercise.

7 Claims, 12 Drawing Sheets

TANNING CHAIR

SUMMARY OF THE INVENTION

The object of the present invention is a chair which is particularly meant for being associated with a tanning apparatus.

Known in the field of artificial tanning is to have a face tanning apparatus associated with a more or less comfortable chair for a user to sit thereon. It is further known to have a body tanning apparatus associated with a couch for a user to lie thereon.

By the former and the latter combination that are usually on the market, a buyer—which may be the owner of one of the many tanning parlours, for example, is compelled to meet a difficult alternative, since the buyer has to choose whether to buy both of such combinations, with a considerable expenditure of money, or of making the decision of buying only one of them, and in so doing, the buyer will be greatly limited from an operative viewpoint.

The present invention aims to solve thouroughly the above problem, and to this end the same proposes a chair which can be particularly combined with any desired tanning apparatus. The main feature of this chair is that the same can be quickly converted into a comfortable couch, by causing the back, the seat, and the foot-rest of the chair to be moved on to the same horizontal plane.

Thus, it is possible to associate with this chair both a face tanning apparatus and a body tanning apparatus, which affords a great number of advantages.

Preferably by a suitable, generally electric, actuator the parts of the chair are caused to assume different angular positions relative to each other.

According to a further important feature of the chair of the invention, the skeleton of this chair has been so designed as to avoid that a user should uncomfortably slide thereon, when the chair is moved from its upstanding normal position into its horizontal position, and vice-versa.

The chair according to the invention, is provided with a mechanical massage device usually arranged inside the back thereof, which by means of members being imparted an alternating rotary motion, effects a relaxation massage, according to the Shatzu Art. In the same chair vibration massage means are also provided.

According to a still further feature of the invention, the chair carries a face tanning apparatus, which is swingably mounted thereon, so as to be movable, preferably by an electric actuator, from an inactive position to an active position, and vice-versa. This face tanning apparatus is provided with an ionization device located near to face ventilation means, for producing a tonifying and relaxing action to a user.

According to a yet another feature of the said chair, the same is provided with means for causing the body of a user to be rythmically and positively moved, so that the user is enabled to benefit from a passive gymnastic exercise. These means may be applied, for example, to the foot-rest of the chair, so that the user's legs will be subjected to an alternating movement.

The said chair also comprises means for heating the back and/or the seat thereof, as well as some small devices which are made available to a user for checking his or her tanning condition, the hydration of his or her skin, and his or her stress level.

The chair according to the invention may be provided with a plurality of fixtures, and may, for example, comprise a stereophonic radio receiver and sound reproduction system, with the relative loudspeakers being incorporated into the chair itself.

These and other features of the chair according to the invention, and the advantages arising therefrom, will clearly appear from the following detailed description of some preferred embodiments thereof, which are made by way of some non-limiting examples, and are shown in the accompanying sheets of drawing.

DESCRIPTION OF THE PREFERRED EMBODIMENTS

Figure 1:
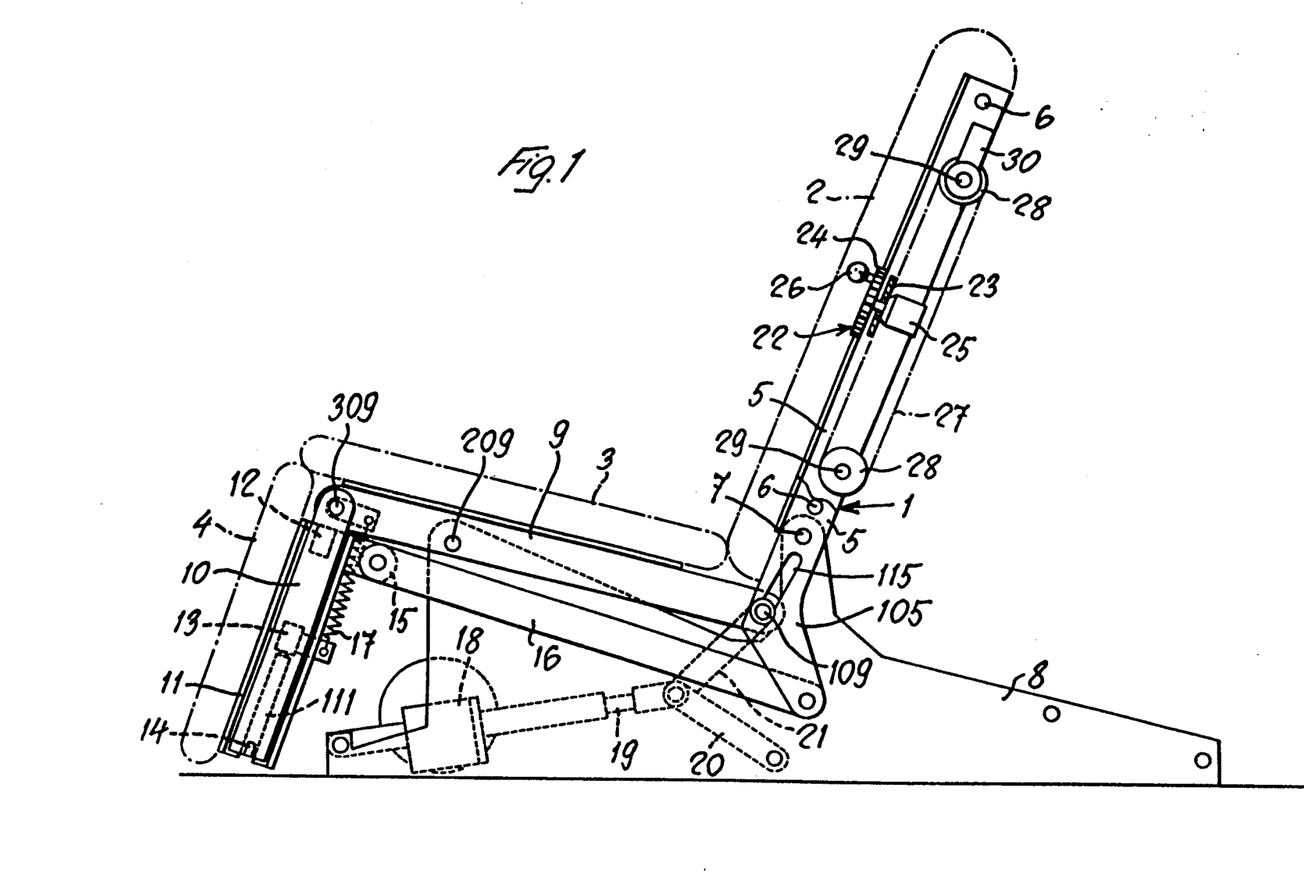
FIG. 1 is a side view of the skeleton of a chair according to the invention, shown in its upstanding normal position.
Figure 2:
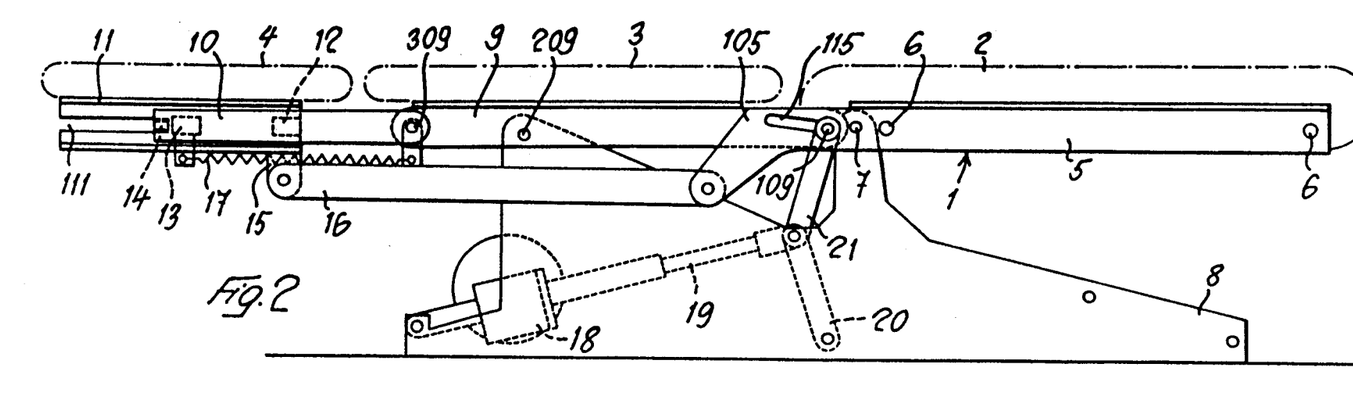
FIG. 2 is a side view of the said skeleton, shown in its horizontal position.

Referring to FIGS. 1 and 2, there is shown that a chair according to the invention, which is convertible into a couch, and is preferably meant for being associated with any tanning apparatus, comprises an articulated skeleton, designated as a whole by numeral 1, which supports the back 2, the seat 3, and the foot-rest 4 of the said chair.

Of said skeleton 1, that part which supports the chair back 2, consists of a frame formed by two side members 5 preferably having a "T" profile, which by means of suitable crosspieces 6 are rigidly connected to each other, and are fulcrumed about a common shaft 7 carried by the base frame 8 of the chair. The terminal section 105 of said side members 5, which is directed toward the seat 3, is flat, and its downward end portion is conveniently bent at an angle. In this section 105 an elongated slot 115 is formed, which is substantially in line with the longitudinal axis of member 5, and a pivot 109 which is secured to one end of a respective lever 9, is slidably engaged in the said slot. Both levers 9 which are for supporting the seat 3 of the chair, are pivotally connected at 209 to the base frame 8 thereof, and carry a respective bar 10 which is pivotally connected to the opposite end of said levers 9. Both bars 10 are in turn so engaged in respective section irons 11 interconnected by crosspieces 12 and 13, as to be longitudinally slidable therein. Also the bars 10 can be rigidly connected to each other by a crosspiece 14, and, in this case, a suitable longitudinal slot 111 however needs to be formed in the section irons 11, to permit the sliding movement of the said crosspiece 14. Both section irons 11 which support the chair foot-rest 4, carry at their end which is adjacent to the pair of levers 9, a downwardly turned ear 15 which through a respective arm 16, is connected to the end of section 105 of the respective side member 5. A cylindrical spiral spring 17 fitted between the crosspiece 13 and the shaft 309 pivotally connecting the bars 10 to the levers 9, tends to keep the section irons 11 drawn near to the said levers 9.

An electric actuator 18 is provided for moving the articulated skeleton 1, and the casing of the said actuator 18 is firmly connected to the base frame 8, while its driving rod 19 is connected to one end of two pairs of lever arms 20 and 21, the opposite ends of the lever arm pair 20 being pivotally connected to the base frame 8, and the opposite ends of the lever arm pair 21 being fulcrumed about pivots 109.

Thanks to the above described articulated skeleton of the chair, and to the relative means for angularly moving the parts thereof, a chair according to the invention can be so operated as to be moved from its upstanding normal position (see FIG. 1) into a horizontal position, in which the same is converted into a couch (see FIG. 2), and vice-versa, thus avoiding that a user should undesirably slide on the chair.

In a chair in which its back and its foot-rest are pivotally connected to the chair seat by means of fixed pivots, it is actually known that when the chair back and foot-rest are swung into their horizontal position, the back of the chair is, on the one hand, drawn away from the chair seat and, on the other hand, the chair foot-rest is drawn near thereto, which results in the bust, the head, and the legs of a user being subjected to a troublesome sliding movement on the said parts of the chair.

Thanks to the articulated skeleton 1, such an inconvenience is removed, since the said skeleton is provided with linkages and with kinematic connections between its members, such that any relative sliding movement between the back and the seat of the chair, and between the seat and the foot-rest thereof, are avoided.

Figure 3:
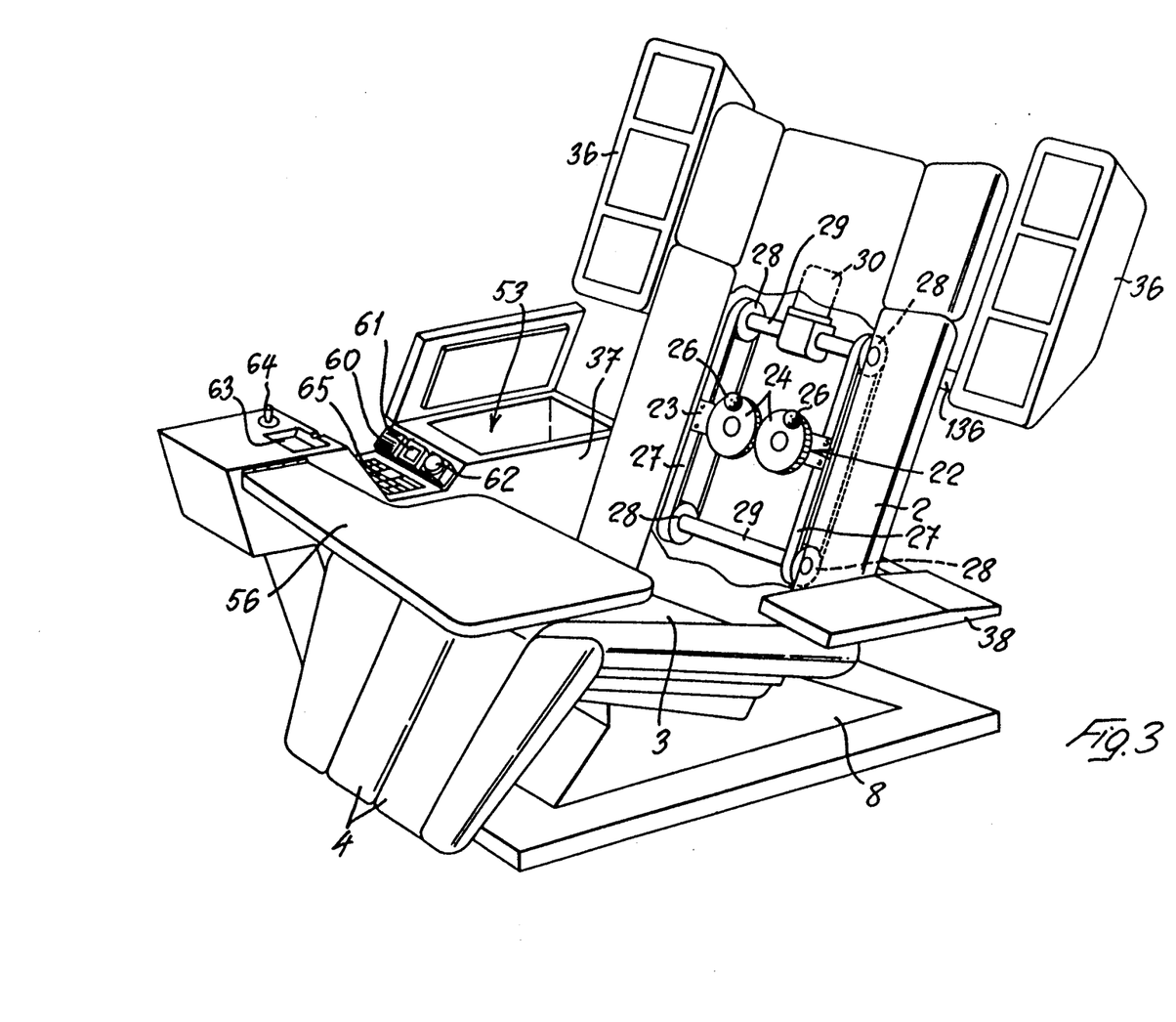
FIG. 3 is a perspective view of a chair according to the invention, with the back thereof being partly opened, to display the mechanical massage device which is incorporated thereinto.

Referring to FIGS. 1 and 3, there is shown that a chair, according to the invention, comprises a mechanical massage device designated as a whole by 22. This device consists of a supporting plate 23 on which two intermeshing gear wheels 24 are mounted, and one of these gear wheels is driven by a small geared motor 25 which is fixed to the said plate 23. Each gear wheel 24 carries an eccentric knob 26 which is freely rotatably fitted thereon. The eccentricity of the two knobs 26 on gear wheels 24 must be such that the said knobs 26 will by no means interfere with each other.

Figure 11:
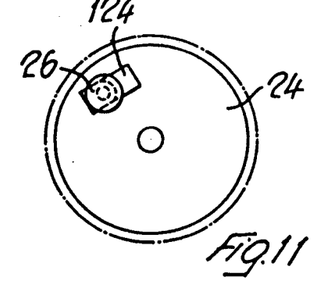
FIGS. 11 and 12 show a modified embodiment of the mechanical massage device which is incorporated into the back of the chair.
Figure 12:
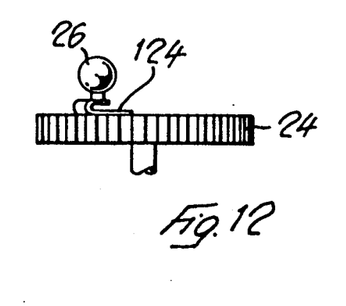

According to FIGS. 11 and 12, the knobs 26 can be fitted on the gear wheels 24 even in a sprung manner, which is good for a higher gentleness of the massaging action. In this case, the knobs 26 are freely rotatably fitted on the free side of a U-made flat spring 124 having its opposite side secured to the gear wheel 24. The U-made flat spring 124 is so arranged that its longitudinal expanse is oriented tangentially to a circle which is concentric to the gear wheel 24, and its open side lies opposite to the direction of rotation of the respective gear wheel 24.

Preferably, the mechanical massage device 22 is incorporated into the back of the chair, and is imparted an alternating motion along the back thereof. Therefore, the plate 23 is fixed between two toothed belts 27 stretched between two pairs of pulleys 28, which in turn are keyed onto respective shafts 29 for driving in rotation the said pulleys, one of these shafts 29 being directly connected with an electric actuator 30. The shafts 29 and the actuator 30 are carried by the frame supporting the back of the chair.

The said device 22 is so housed inside the back of the chair, as to allow the counter-rotating knobs 26 to perform their massaging action on the back of a user, through a less thick strip of the chair back upholstery. The layer of this strip which directly contacts the said knobs, is made from a low friction material, whereby to prevent an undesired heating of the chair back upholstery.

The mechanical massage device 22 may be also provided in form of a self-standing fixture of the chair. In this instance, the device is housed in a special container and is put at a user's disposal, that can use the same on any part of his or her body.

Figure 4:
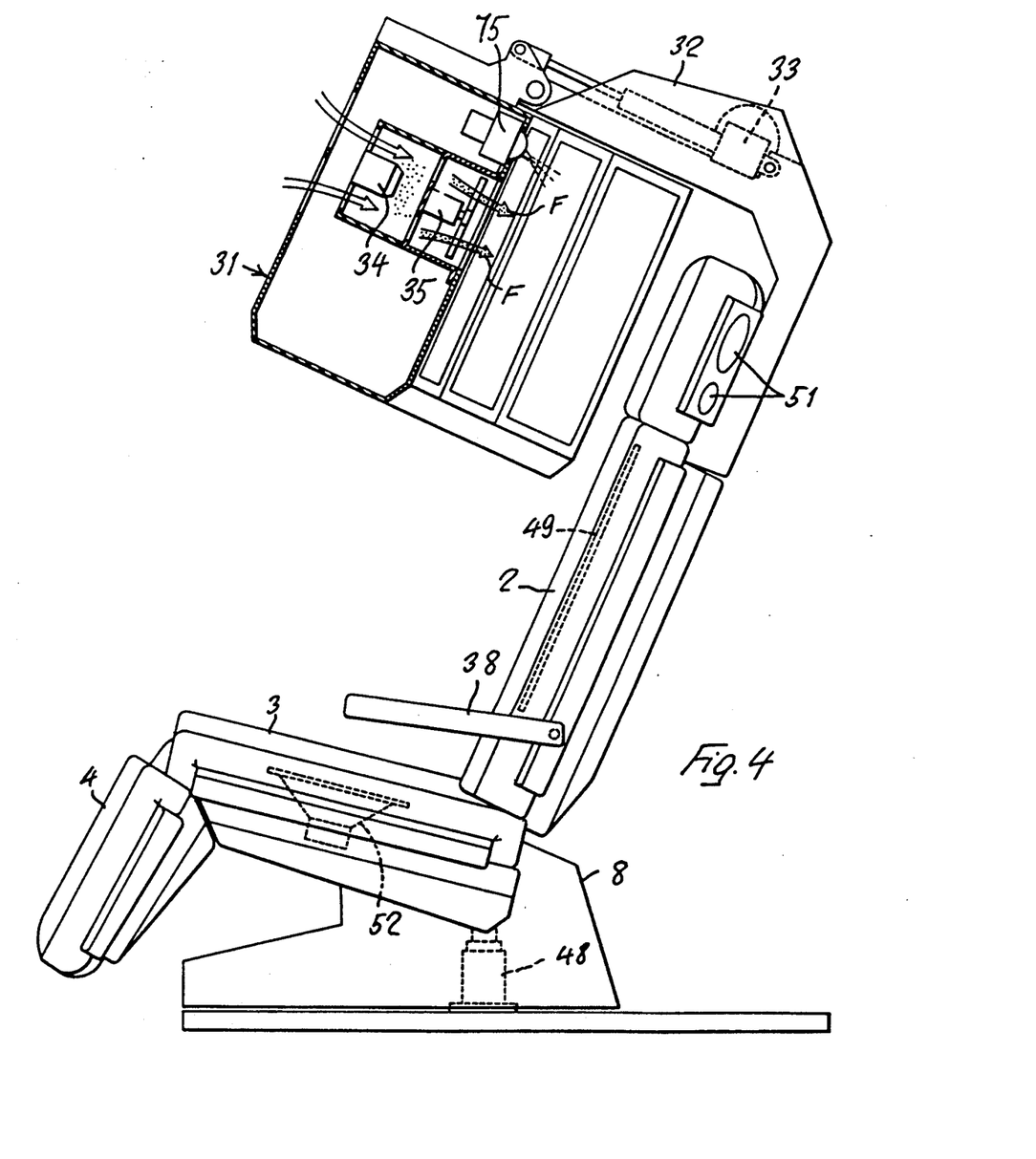
FIG. 4 is a side elevational view of the said chair.

Referring to FIG. 4, there is shown that a chair according to the invention, may comprise an apparatus 31 for tanning the face and may be the top portion of the bust of a user. This apparatus is carried by the chair through an arm 32 extending over the back of the chair. Preferably, the tanning apparatus 31 is hingedly connected to the end of said arm, so that it can be moved by an electric actuator 33 from an inactive upper position, into an active lower position shown in said FIG. 4, and vice-versa.

Since it was ascertained that a tanning apparatus generates per se positive ions, and that these positive ions induce a stress condition in a user, the invention provides for associating with the said apparatus 31 a device 34 which is apt to emit a great quantity of negative ions, that neutralize the said effect on the user. This ionization device 34 is arranged immediately upstream of the face ventilation means designated by numeral 35, when referring to the direction of the air flow produced by the said means. Thus, the fresh air flow F enriched with negative ions, flows on, and relaxes the face of the user. Moreover, to cool the user and to hydrate the skin of his or her face, the chair according to the invention may also comprise an atomizer nozzle 75 for atomizing water, or any desired hydrating liquid. To this end, the chair may comprise a reservoir and a nozzle-feeding system, which are not shown here in detail. Preferably, the atomizer nozzle 75 is arranged over the face ventilation means 35, and is adjustable. The control for the nozzle may be of the electric or the pushbutton type, and may be located even near the said nozzle.

A chair according to the invention may also comprise an apparatus for tanning the hands and may be the arms of a user. Some possible different embodiments of that apparatus for tanning teh hands and may be the arms of a user are diagrammatically shown in FIGS. 3, 15, 16, 17, 18. According to FIG. 3, this apparatus consists of two separate units 36 which are hingedly connected at 136 to the sides of the chair back 2, and which are movable, generally by a suitable actuator (not shown), from an inactive, subvertical position to an active, substantially horizontal position, above the arms 37 and 38 of the chair.

Figures 13, 17:
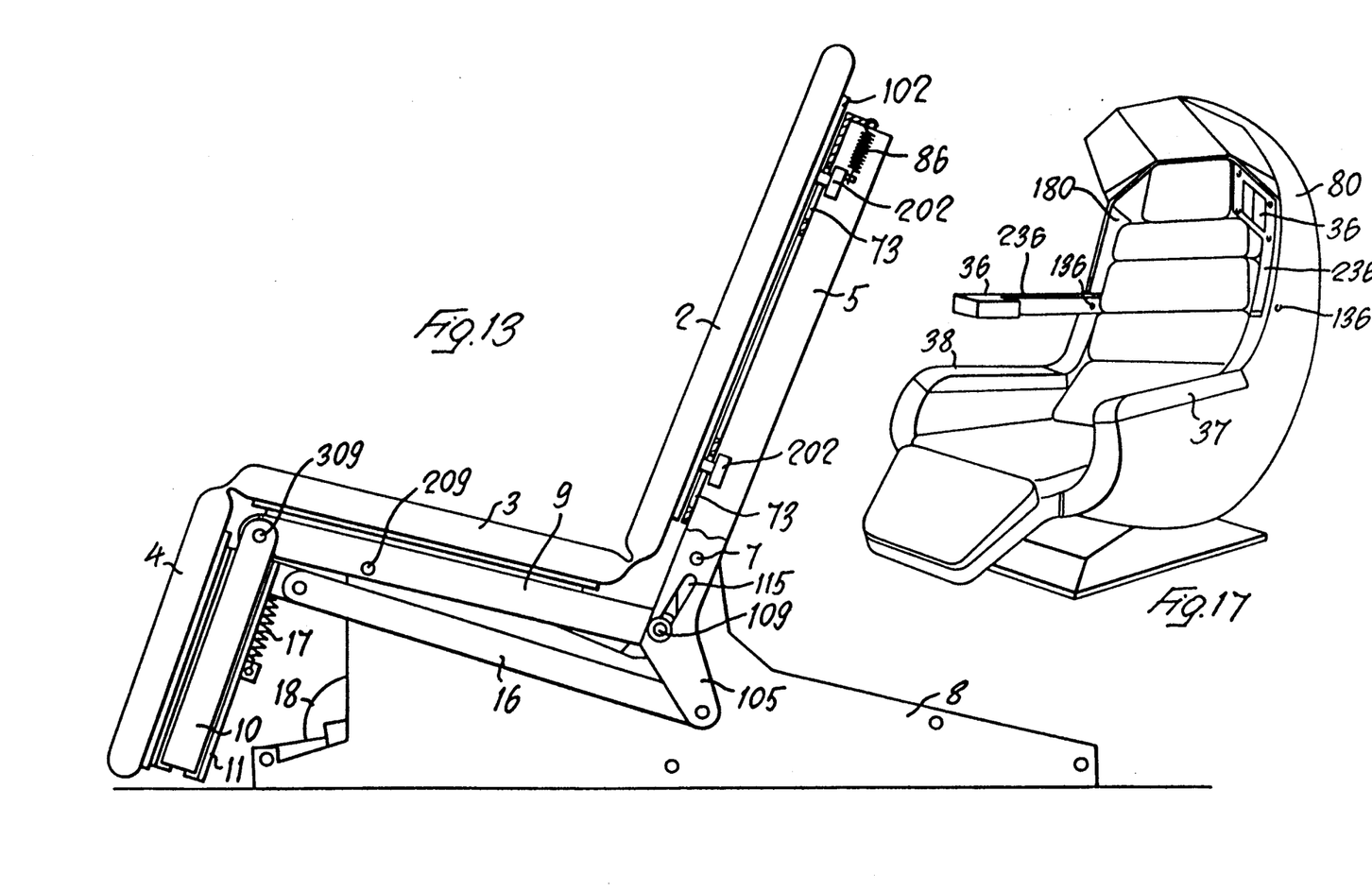
FIGS. 13 and 14 show a side view of a third embodiment of the skeleton of a chair according to the invention.
FIGS. 15 to 18 show some further embodiments of the apparatus for tanning the hands and maybe the arms.

According to the embodiment shown in FIG. 17, each separate unit 36 is secured at the free end of an arm 236. In their inactive subvertical position the units 36 and their supporting arms 236 are fitted completely in corresponding recesses 180 of an external housing 80 of the chair.

Figure 15:
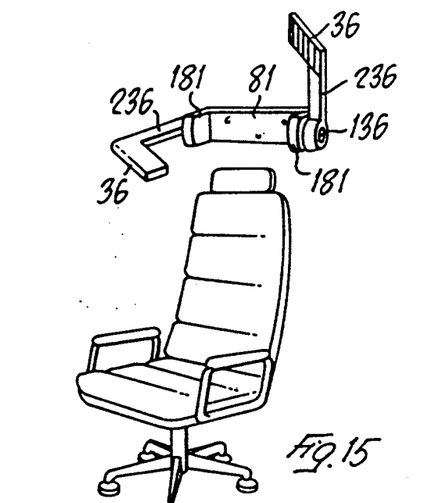
Figure 16:
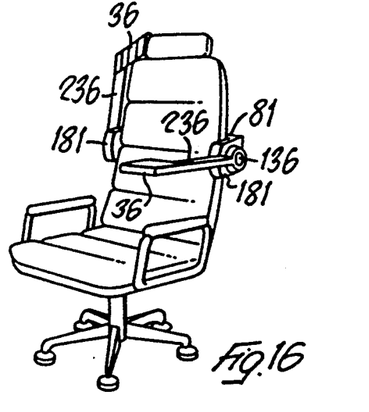

The apparatus for tanning the hands and may be the arms of a user shown in FIGS. 15 and 16 is built as a separate unit, which can be secured to the rear side of the back of chair. The separate units 36 and their supporting arms 236 are hingedly connected each one to one of the two free side-walls 181 of a u-shaped bracket 81 which surrounds the rearside and the two sides of the chair.

Figure 18:
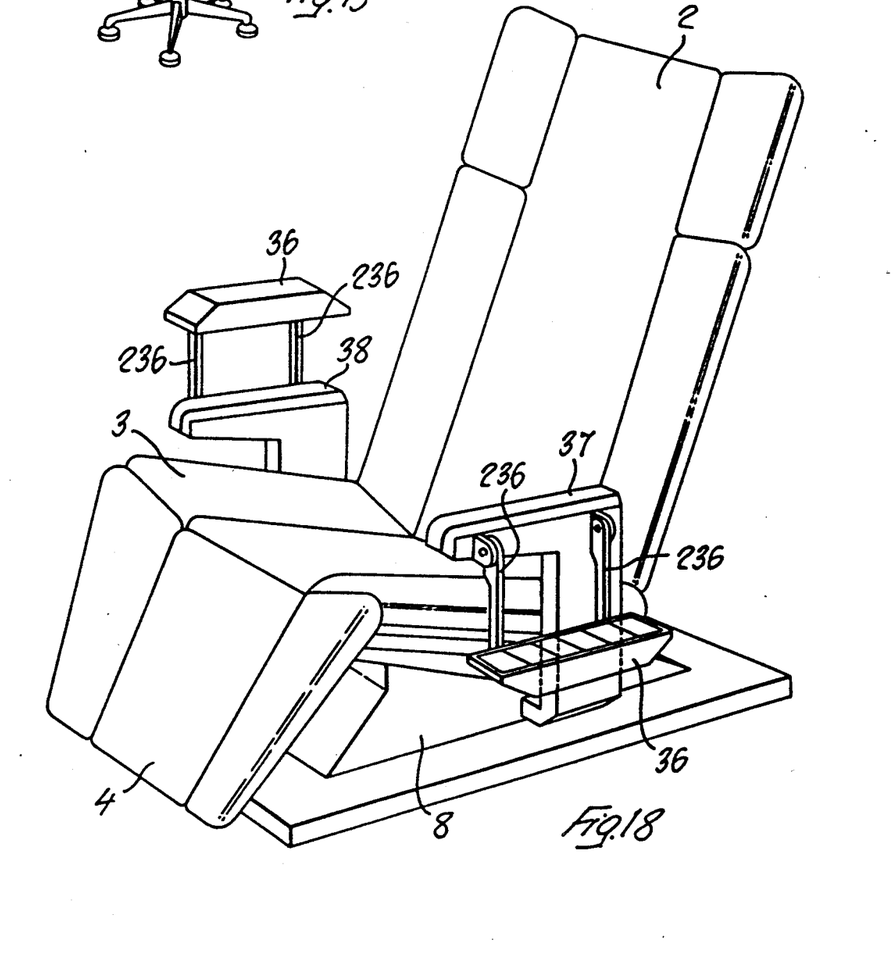
Figure 19:
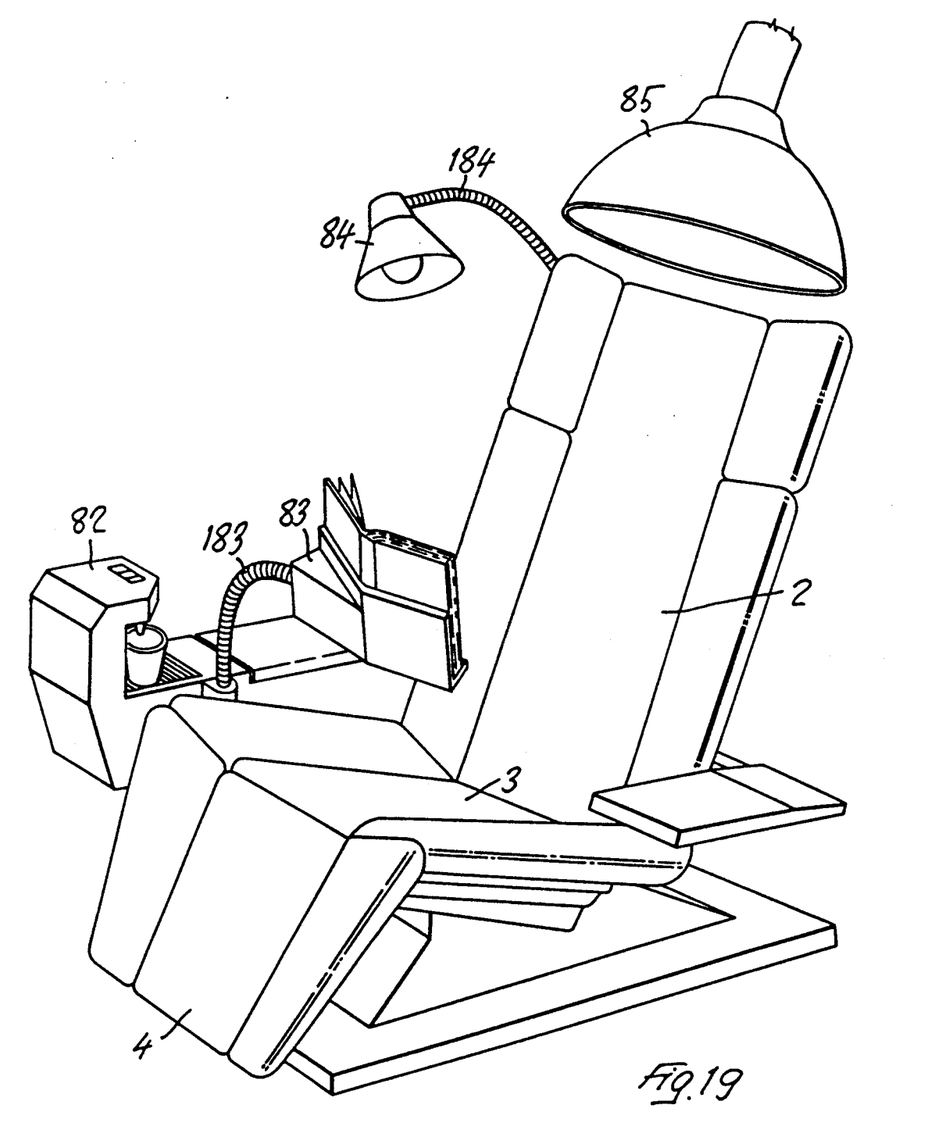
FIG. 19 is a perspective view of a chair according to the invention in which some further fixtures therefore are shown.

In a further embodiment of the appartus for tanning the hands and may be the arms of a user according to FIG. 18, each separate unit 36 is pivotally connected with the external side of an arm 37, 38 of the chair. Each unit 36 is provided with two parallel arms 236 which are connected to the external side of the associated arm 37, 38 so as to pivot around a common axis parallel to the associated arm 37, 38 of the chair. The arms 236 are perpendicular to the radiating surface of the units 36. Thus the units 36 are swingable from a inactive position in which the units 36 are suspended outside the associated arm 37, 38, with their radiating surface directed upwardly to an active position in which the units 36 are placed above the associated arms 37, 38 of the chair whith their radiating surface directed downwardly to said arms 37, 38 of the chair.

Figure 5:
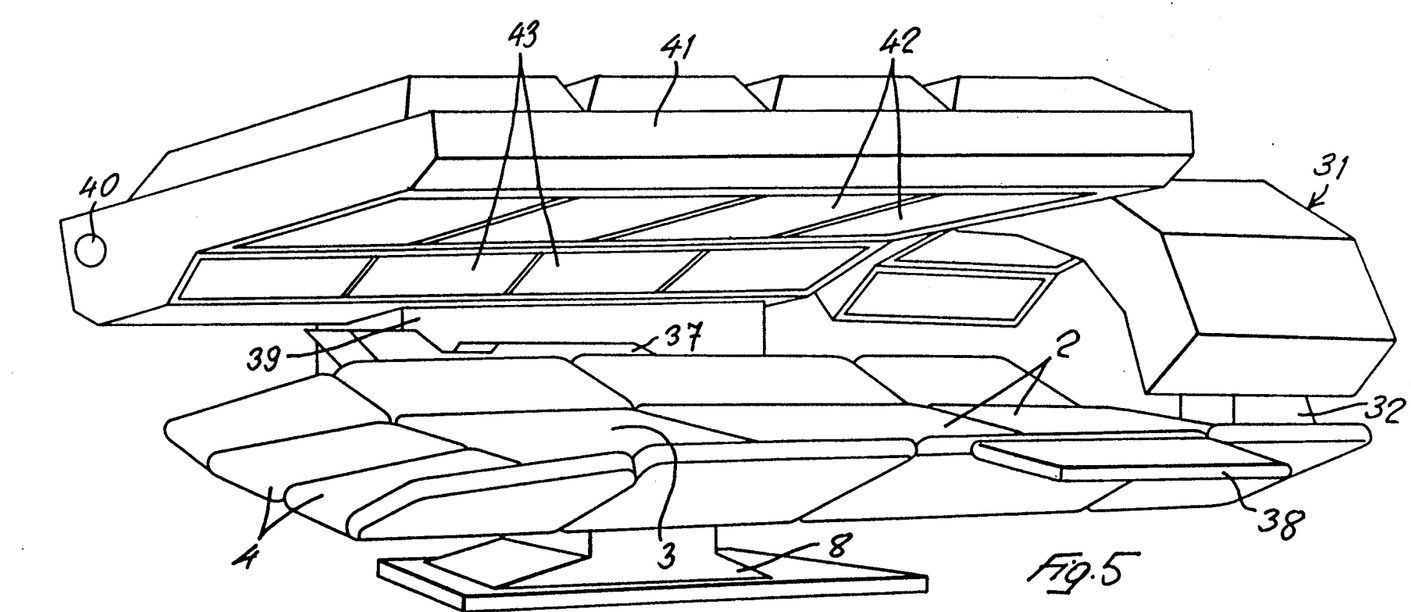
FIG. 5 is a perspective view of a chair according to the invention, arranged in its horizontal position in the manner of a couch, and operatively associated with a face and a body tanning apparatus.

A chair according to the invention may further comprise a body tanning apparatus, the use of which requires the said chair to be set into its horizontal position, in the manner of a couch, as shown in FIG. 5. This apparatus comprises a base frame 39 carrying a frame 41 which is hinged on a horizontal shaft 40, and which houses the two sets of front and lateral tanning lamps 42 and 43. The provision on the swingable frame 41 of the lateral lamps 43 helps a better tanning of a user's hips.

Figure 6:
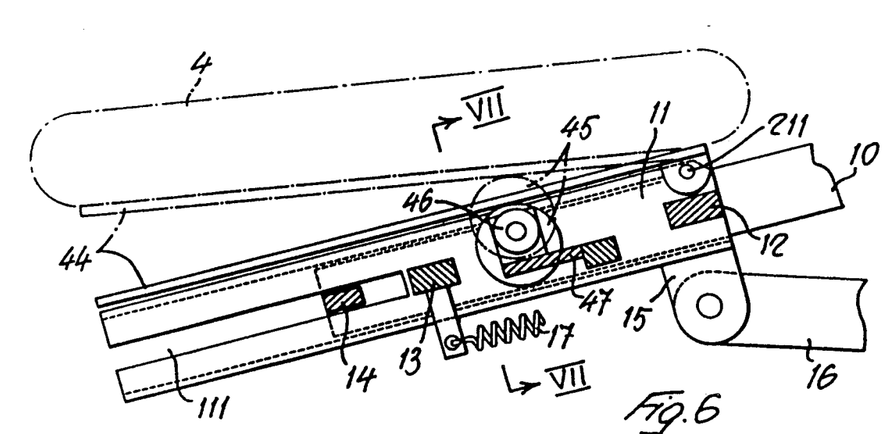
FIG. 6 shows the foot-rest of the said chair, with a device for a passive gymnastic exercise being applied thereto.
Figure 7:
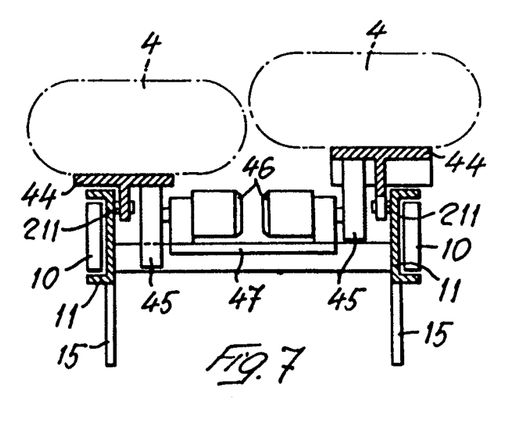
FIG. 7 is a cross-sectional view, taken on line VII—VII in FIG. 6, of the said foot-rest.
Figure 8:
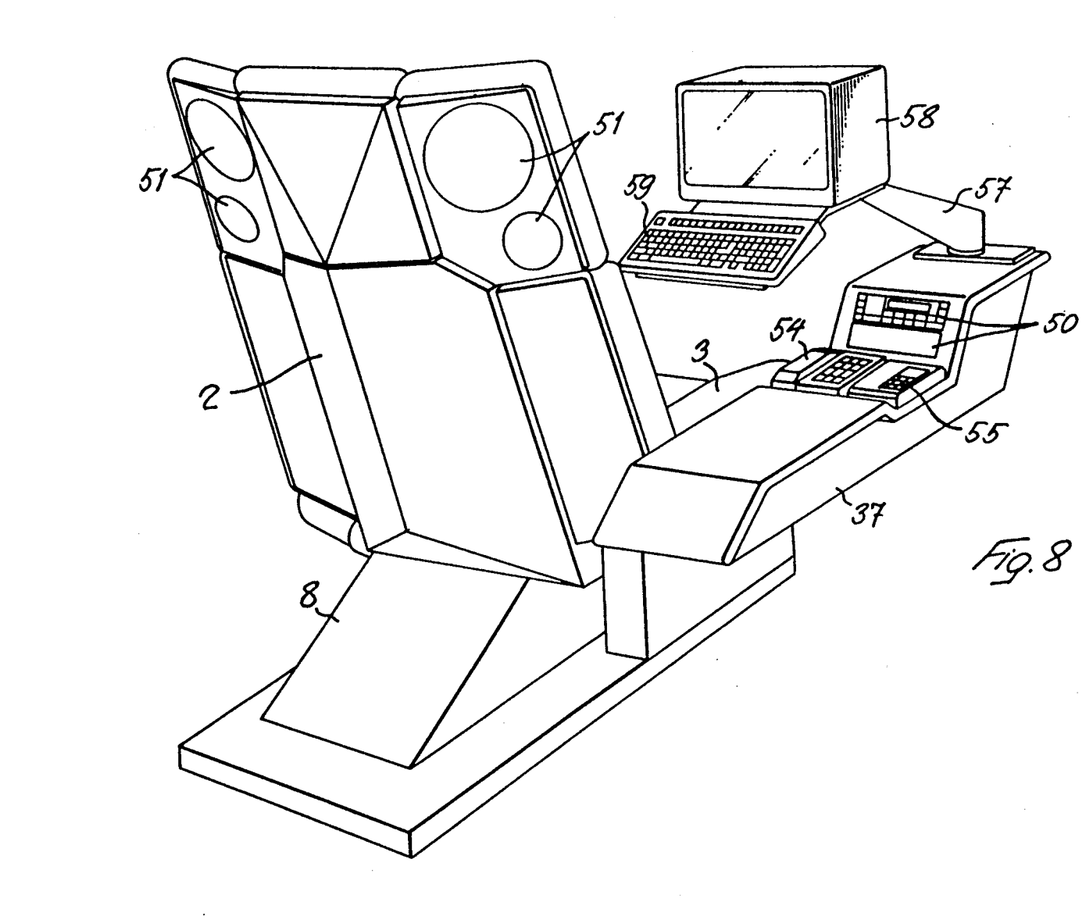
FIG. 8 is a perspective rear view of a chair according to the invention, in which some fixtures therefor are shown.

A further feature of the chair according to the invention, is that this chair may be provided with means for subjecting a user to a passive gymnastic exercise according to any art. According to one embodiment shown by way of an example in FIGS. 6 and 7, the said means comprise a device which is applied to the frame (11, 12, 13) supporting the foot-rest 4 of the chair. This quite simple device consists of two flat ledges 44 which are hingedly connected by one end at 211 to the respective section irons 11, on which the ledges rest. These ledges 44 with the two separate foot-rest members being respectively fixed thereto, are engaged from their underside by a relative rotary cam 45 causing the ledges to be alternatingly oscillated, so that the legs of a user are compelled to perform the same movement as the separate foot-rest members. The cams 45 are operated by respective electric motors 46 carried by a small frame 47 fixedly arranged between the section irons 11. As an alternative, the said device can be simply used for changing at will the angular position of the foot-rest, relative to the seat of the chair, by properly actuating the motors 46.

A chair according to the invention may be provided with a hydropneumatic or electric device 48 (see FIG. 4) allowing to vary as desired the chair level from the floor.

The said chair may be further provided with heating means 49, for example inserted into the chair back 2.

A number of fixtures may be associated with the chair according to the invention, among which (see FIGS. 3, 4, 8 and 19):

- a stereophonic radio receiver and sound reproduction system 50 housed in the fixed arm 37 of the chair, and provided with the relative loudspeakers 51 and 52, the loudspeakers 51 being mounted, may be in an orientable manner, on the chair back 2, and the loudspeaker 52 being arranged under the chair seat 3,
- a refrigerated cabinet for drinks 53, also accomodated in the arm 37 of the chair,
- a telephone 54 and the relative call-recording device 55 also located on the said arm 37,
- a tiltable service table 56, and a turnable arm 57 for supporting a video 58, and may be a keyboard 59, which are both carried by the said arm 37,
- the devices 60, 61, and 62, which are respectively for measuring the tanning condition, the skin hydration condition, and the stress level of a user, which are accomodated as well in the said arm 37,
- an ashtray 63 and a lighter 64.
- a drink dispenser 82,
- a lectern 83, preferably supported by an articulated arm 183,
- a lamp for reading purpouses 84, preferably supported by an articulated arm 184,
- a hood 85, being mounted above the upper end of the back of the chair.

The control board 65 may be also located on the arm 37 of the chair.

The loudspeaker 52 arranged under the seat of the chair, may also perform a vibratory massaging function, at a very low frequency.

Of course, a chair according to the invention, may be placed in any room, and may be used for any desired purpose. This chair may be just useful in a dentist's surgery or in a beauty parlour, or the same may be installed on board of an aircraft.

From the foregoing, it is apparent that a chair according to the invention, affords quite a number of advantages, among which:

- the possibility of converting the chair into a comfortable couch, while avoiding that a user should be subjected to a tiresome sliding movement on the chair back and seat,
- a massaging action,
- a passive gymnastic exercise,
- the rational use of an apparatus for a complete tanning of the body of a user,
- the provision of a number of fixtures.

Of course, the invention is not limited to the embodiment as disclosed above, and numerous changes and modifications may be brought to the same, the more so in construction.

Figure 9:
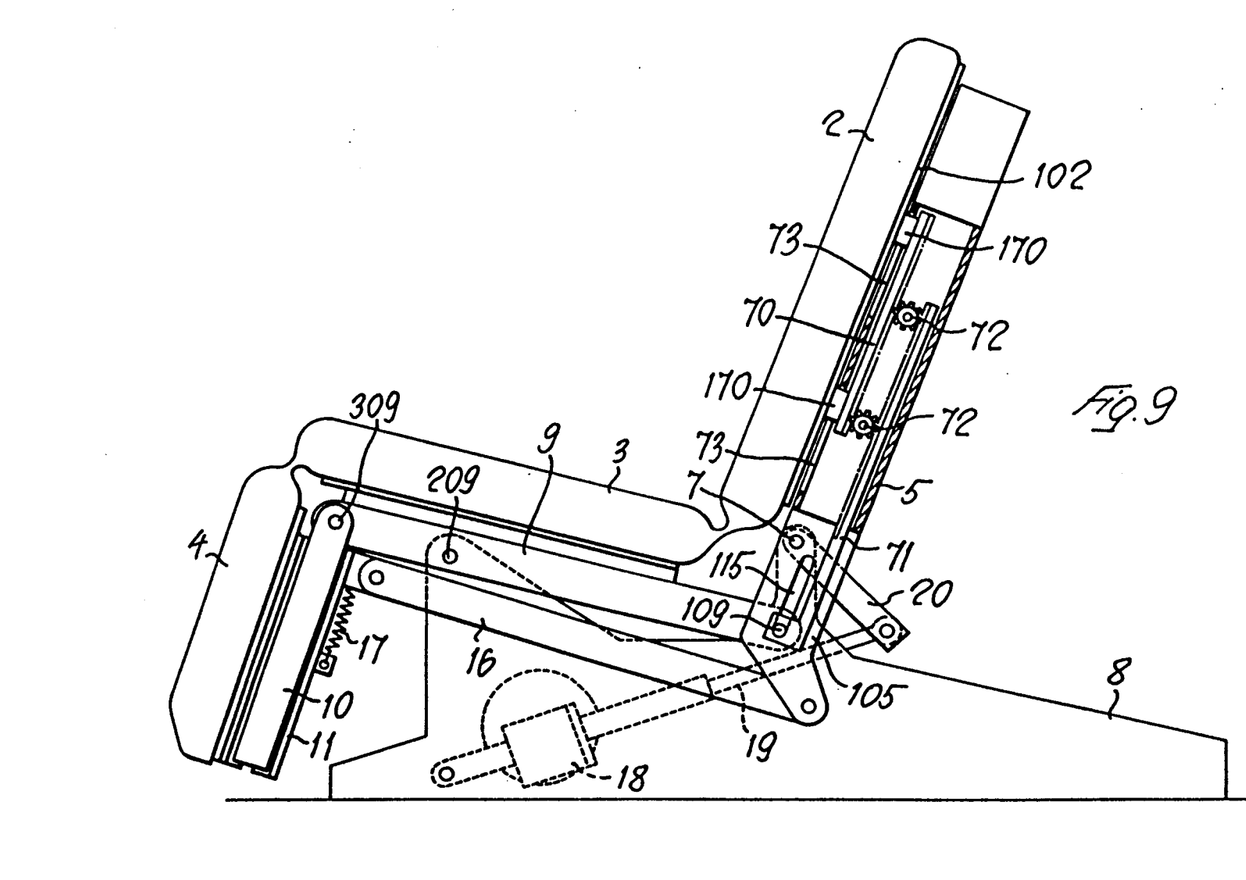
FIG. 9 is a side view of a second embodiment of the skeleton of a chair according to the invention.
Figure 10:
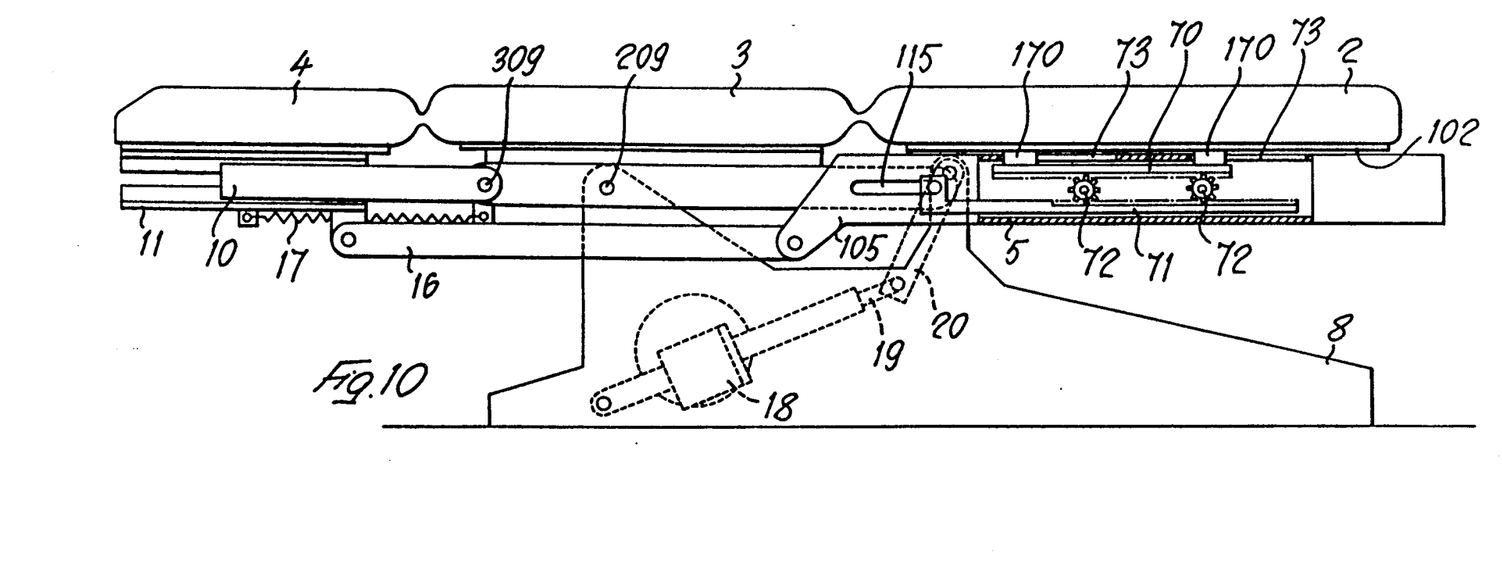
FIG. 10 shows the skeleton according to FIG. 9, in horizontal position.

In FIGS. 9 and 10 there is shown a second embodiment of the skeleton of the chair according to the invention, which affords the possibility of entirely and efficiently recovering the gap between the back and the seat of the chair, arising from the chair back being swung from its substantially upright position into its horizontal position. Therefore, the chair back 2 is not supported directly by the frame consisting of the side members 5 interconnected by the crosspieces 6, and being swingably mounted on the base frame 8, but the chair back 2 is here provided with a further suporting frame, generally designated by 102, which is so assembled as to be slidable toward the seat 3, on the frame 5, 6 that is swingably mounted on the base frame 8 of the chair. In this second embodiment, the frame 5, 6 that is swingably mounted on the base frame 8 of the chair, is similar to the frame according to the embodiment shown in FIGS. 1 and 2. The side members 5 of this frame are tubular members, and are also provided with wings 105 having an elongated slot 115 therein.

The tubular side members 5 are still fulcrumed about the common shaft 7 carried by the base frame 8. Two facingly arranged racks 70, 71 are fitted in the tubular sections of the side members 5, so as to be slidable on the opposite sides of the said tubular sections. The two facingly arranged racks 70, 71 are connected to each other through interposed pinions 72 in meshing engagement therewith, which are freely rotatably supported on the inner wall of the side members 5 tubular sections. The rack 70 which is contiguous to the chair back 2, is secured to the slidable frame 102 supporting the chair back 2 by means of projections 170 extending through an elongated slot 73 in the respective side member 5, the said elongated slots 73 in the side members 5 being formed according to the sliding direction of rack 70. By their ends lying substantially at the level of the chair seat 3, the racks 71 are fulcrumed about the pivots 109 of levers 9, and similarly to the embodiment according to FIGS. 1 and 2, the said pivots 109 are still engaged in the elongated slots 115 in the flat sections of the side members 5. The electric actuator 18, which is for angularly moving the skeleton (1) of the chair, has its rod 19 connected to the free end of a pair of lever arms 20, and the opposite ends of the lever arms 20 are secured to the common shaft 7, so as to be rotatable together with the said common shaft. When the common shaft 7 is rotated in the direction for swinging into its horizontal position the chair back 2, the pivots 109 are caused to slide in the associated slots 115, away from the chair seat 3, so that also the racks 71 are at the same time caused to correspondingly slide in the tubular side members 5. Such a sliding movement of racks 71 produces an equal sliding movement directed near to the seat 3, of the racks 70, and so of the chair seat 2 being supported thereby. Thus, the gap between the seat 3 and the back 2 of the chair is entirely recovered, which would otherwise not occur with a construction according to the prior art.

Figure 14:
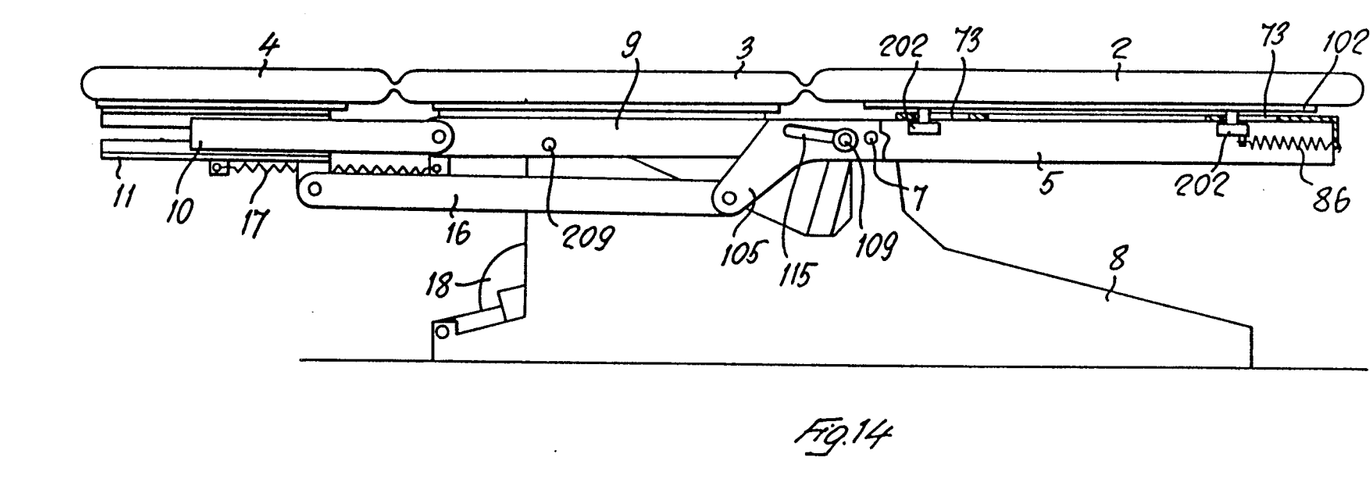

A third embodiment of the skeleton of the chair is shown in FIGS. 13 and 14. This embodiment shows the same advantages of the previous second embodiment according to FIGS. 9 and 10, having a simpler construction.

The skeleton of the chair according to FIGS. 13 and 14 is built substabtially in the same way as the skeleton according to the embodiment shown in FIGS. 1 and 2. The only differences consist in the fact that the back of the chair is slidably supported on a frame as in the embodiment according to FIGS. 9 and 10.

The upholstery of the back 2, of the seat 3 and of the foot-rest 4 of the chair are connected together at their facing edges. The back 2 of the chair is secured to a frame 102, which slides freely on the side members 5. The frame 102 has projections 202 extending through associated elongated slots 73 of the side members 5. The upper projections 202 are connected with the upper free ends of the side members 5 by a spring 86. When the back 2 of the chair is swung in a horizontal position, the freely slidable frame 102 slides on the side members 5 being held in its position relative to the seat 3 by the upholstery, thus preventing the back 2 and the seat 3 of the chair to move away from each other and to execute any relative movement in respect to the body of the user. When the back 2 of the chair is swung from the horizontal position into a substabtially vertical position, the frame 102 slides in the opposite direction with the help of the spring 86.

We claim:

1. A chair for supporting a user undergoing ultraviolet light treatment for inducing body tanning comprising: conversion means for reclining said chair into a couch-like support; a body tanning apparatus mounted on a side of the chair, said body tanning apparatus including a base frame; an overlying case hingedly mounted on said side of the chair; front and side ultraviolet lamps, said lamps being housed in said overlying case.

2. The chair according to claim 1 further comprising a face tanning apparatus and adjusting means for orienting said face tanning apparatus in the direction of the face of a user of said chair.

3. A chair according to claim 2, in which the face tanning apparatus is attached to the chair.

4. A face tanning apparatus according to claim 3, wherein the face tanning apparatus is hingedly connected to one end of an arm located on the back of the chair so that the face tanning apparatus is moveable between an inactive upper position and an active lower position.

5. A chair for supporting a user undergoing ultraviolet light treatment for inducing body tanning, comprising: conversion means for reclining said chair into a couch-like support; a body tanning apparatus mounted on the chair, said body tanning apparatus including a base frame, said base frame including an articulated skeleton with a back, a seat and a footrest, said skeleton including means for allowing the chair to move between a normal upright chair position and an essentially coplanar horizontal couch position without the chair parts being subjected to substantial sliding movement relative to each other, said skeleton comprising a substantially quadrangular frame supporting the back of the chair, said quadrangular frame being pivotally connected to the base frame and provided at its side facing the chair seat with two substantially spaced apart, downwardly extending wings which are bent at an angle to each other and have an elongated slot formed therein and are substantially in line with side members of the frame, a pair of levers supporting the chair seat and pivotally connected to the base frame, one end of the levers carrying a pivot which is slidably engaged in the elongated slot of said wings, and the opposite ends of the levers carrying a bar, a pair of section irons slidably fitted on the bars for mounting a foot-rest of the chair, said section irons being rigidly connected to each other through at least one crosspiece and being provided at their ends adjacent the levers with a downwardly turned ear connected to the respective wing, spring means for connection of said section irons to said levers and for biasing the section irons toward the levers, and including an electric actuator means housed in the base frame of the chair which is connectable to the pivots carried by the levers, the said pivots being engaged in the slots in the wings of the base frame.

6. A chair for supporting a user undergoing ultraviolet light treatment for inducing body tanning, comprising: a base frame, means for converting the chair into a couch, a body tanning apparatus mounted on the chair, and a mechanical massage means arranged within the back of the chair, said mechanical massage means comprising a support plate for a pair of intermeshing gears having a respective rotatable massage knob which is eccentrically fitted thereon, one of the gears being motor driven, and the support plate being fixed between two belt means which are longitudinally stretched relative to the back of the chair between two pairs of pulleys which are in turn keyed onto respective shafts for driving rotation of the pulleys, one of said shafts being motor driven, said counter-rotating knobs capable of performing a massaging action on the user's back through a relatively thin strip of upholstery in the back of the chair.

7. A chair according to claim 6, wherein the layer of upholstery strip which directly contacts the knobs is made from a low friction material.

* * * * *